Figure 1:
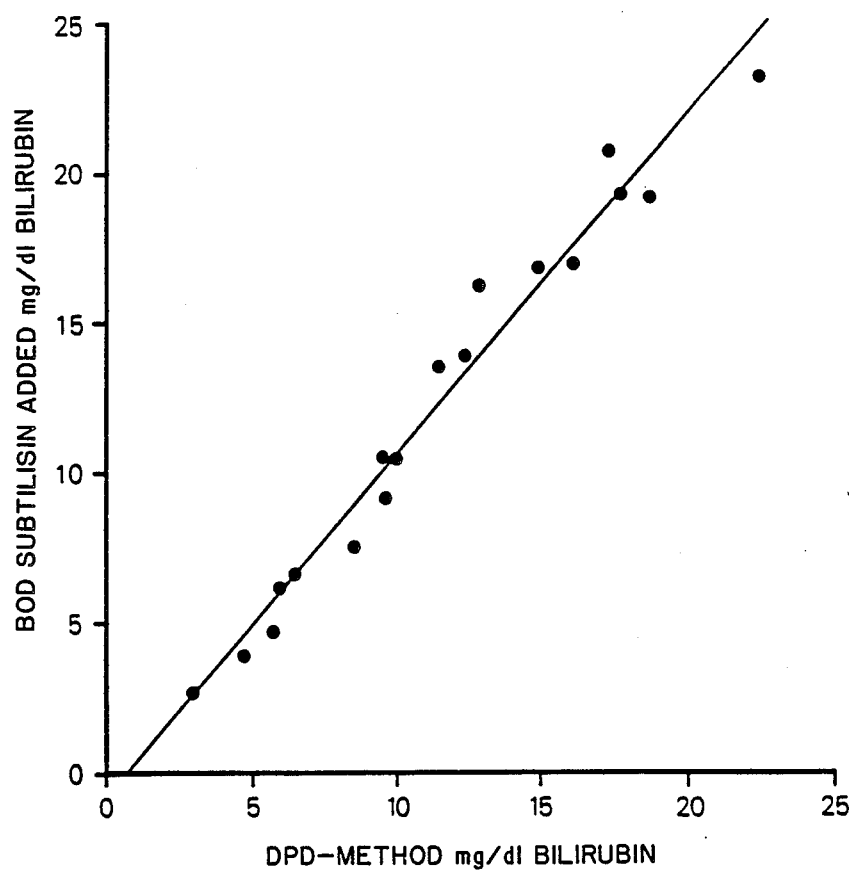

United States Patent [19]

Kruse-Müller et al.

[11] Patent Number: 4,895,799
[45] Date of Patent: Jan. 23, 1990

[54] PROCESS AND REAGENT FOR THE DETERMINATION OF TOTAL BILIRUBIN

[75] Inventors: Cornelia Kruse-Müller, Tutzing; Joachim Siedel, Bernried; Joachim Ziegenhorn, Starnberg, all of Fed. Rep. of Germany

[73] Assignee: Boehringer Mannheim GmbH, Mannheim, Fed. Rep. of Germany

[21] Appl. No.: 17,662

[22] Filed: Feb. 24, 1987

[30] Foreign Application Priority Data

Mar. 14, 1986 [DE] Fed. Rep. of Germany ....... 3608453

[51] Int. Cl.$^4$ ................... C12Q 1/34; C12Q 1/26; C12Q 1/36
[52] U.S. Cl. ........................ 435/18; 435/23; 435/24; 435/25; 435/810
[58] Field of Search ............... 425/10, 23, 24, 25, 425/177, 18

[56] References Cited

U.S. PATENT DOCUMENTS

| 4,251,681 | 2/1981 | Simon | 435/106 |
| 4,378,435 | 3/1983 | Takagi et al. | 435/180 |
| 4,464,468 | 8/1984 | Avrameas et al. | 435/177 |
| 4,554,249 | 11/1985 | Kosaka et al. | 435/10 |
| 4,571,383 | 2/1986 | Takayama et al. | 435/25 |
| 4,600,689 | 7/1986 | Matsui et al. | 435/25 |

FOREIGN PATENT DOCUMENTS 0005637 11/1979 European Pat. Off. .

OTHER PUBLICATIONS

Kosaka et al., Selected Topics in Clinical Enzymology, vol. 2, 1984, pp. 97–107.
Wu, Clinical Biochemistry, vol. 17, Aug. 1984, p. 221–229.
Ohesen et al, Methods in Enzymology, vol. 19, p. 199–215, 1970.
Brisbane et al., Chemical Abstracts, vol. 76, Abstract No. 137763q, 1972, Soil Biol. Biochem., vol. 4, pp. 51–61, 1972.
Lilova et al., Chemical Abstracts, vol. 97, Abstract No. 68405u, 1982, Intl. Conf. Chem. Biotechnol. Biol. Act. Nat. Prod., vol. 3(2), 1981, pp. 391–395.
Pederson et al., Biochemistry, vol. 8, No. 6, Jun. 1969, pp. 2357–2365.

*Primary Examiner*—Esther M. Kepplinger
*Assistant Examiner*—Florina B. Hoffer
*Attorney, Agent, or Firm*—Felfe & Lynch

[57] ABSTRACT

The present invention provides a process for the determination of total bilirubin in samples of body fluids. The method comprises the incubation of a sample of body fluid with both subtilisin which completely liberates bilirubin from its albumin and with bilirubin oxidase as a measurement of total bilirubin content in said body fluid sample.

10 Claims, 2 Drawing Sheets

PROCESS AND REAGENT FOR THE DETERMINATION OF TOTAL BILIRUBIN

The present invention is concerned with a process and a reagent for the determination of total bilirubin by means of bilirubin oxidase.

In the clinical-chemical laboratory, the determination of bilirubin, especially in serum, is an important parameter for the elucidation of various disease symptoms, for example in the case of hepatitis, liver cirrhosis, liver/bile diseases and hemolytic diseases. In the case of neonates, in the first days of life there occurs a so-called physiological jaundice which, in the case of too high bilirubin values, can be lethal or at least give rise to brain-damaging effects (kernicterus).

Bilirubin can be present in the serum adsorptively bound to albumin ($\alpha$-bilirubin), to a sugar residue ($\beta$-bilirubin), to two sugar residues ($\gamma$-bilirubin) or covalently to albumin ($\delta$-bilirubin). $\beta$-plus $\gamma$-bilirubin are referred to as conjugated bilirubin and $\alpha$-bilirubin is referred to as unconjugated bilirubin. The total bilirubin is made up of the $\alpha$-, $\beta$-, $\gamma$- and $\delta$-bilirubins. A detailed description thereof is given in clinical Biochemistry, 17, 221-229/1984.

The determination of total bilirubin can be carried out by the process described by Jendrassik (Biochem. Z., 297, 81/1938). In this case, bilirubin is coupled in the presence of caffeine with diazotised sulphanilic acid to give an azo coloured material. However, this process suffers from numerous disadvantages: on the one hand, the reagent used is very unstable and must be prepared immediately before carrying out the determination. The test is thus difficult to carry out and can only be automated with difficulty. Furthermore, the presence of nitrite in the Jendrassik test, as well as the strongly acidic pH in this as well as in other tests using diazonium salts, gives rise to disturbances in the case of hemolytic sera.

Another method for the determination of total bilirubin is described in Scand. J. Clin. Lab. Invest., 29, Suppl. 126, 1972, Abstract 11.12. In this case, bilirubin is coupled with a diazonium compound to give an azo-bilirubin and the colour formation is measured. The liberation of the non-conjugated bilirubin takes place by the addition of a detergent. In the same way as the Jendrassik method, this determination is also disturbed in hemolytic sera. Since other components of serum, for example indican, can react with diazonium salts, too high values for total bilirubin are often found in uraemic patients.

Another process for the determination of total bilirubin is described in selected Topics in Clinical Enzymology, 2, 97-107/1984. According to this, bilirubin is reacted with bilirubin oxidase (EC 1.3.3.5) and the extinction decrease of the bilirubin is measured at 410 to 480 nm. This process is not disturbed by hemolytic or uraemic sera but it has the disadvantage that the end point of the reaction, depending upon the sample used, is often first achieved after 1 to 2 hours. The essential reason for this may well be that the albumin-bound bilirubin is scarcely accessible to an enzymatic reaction and its dissociation from albumin takes place only very slowly or, in the case of $\delta$-bilirubin, does not take place at all. Consequently, this process is also unsuitable for routine analyses in the laboratory and especially for use in automated systems.

Therefore, frequent attempts have been made so to improve this process that albumin-bound bilirubin is also completely included.

From Federal Republic of Germany Patent Specification No. 32 39 236 there is known a process for the determination of bilirubin with bilirubin oxidase, with the addition of surface-active agents, aromatic carboxylic acids, sulphanilamides or proteases (pronase P). The use of proteases and especially of protease mixtures, such as pronase P, suffers from the considerable disadvantage that these enzymes break down the protein bilirubin oxidase and thus, depending upon the period of storage of the reagent or the incubation time, bring about a reduction of bilirubin oxidase activity. An examination of this process showed that it cannot be used for the complete determination of bilirubin.

From Chemical Abstracts, 102, 20074e, it is known to pre-treat the sample with surface-active agents, as well as with protease and/or lipase, which is not specified in more detail, in order to break down the bond between bilirubin and albumin. According to this, it is possible, with sodium lauryl sulphate (sodium dodecyl sulphate; SDS), admittedly to include substantially more bilirubin (89% of the total bilirubin contained in the sample) than without such additives (19%) but it is still not complete. Thus, this process is also not suitalbe for a quantitative test which can also be used for samples with differing contents of albumin-bound bilirubin.

In Selected Topics in Clinical Enzymology, 2, 97-107/1984 (publ. Walter de Gruyter & Co., Berlin/New York), it is suggested to carry out the determination in the presence of anionic detergents, such as sodium dodecyl sulphate. However, for the complete liberation of albumin-bound bilirubin, very high concentrations of detergent are needed (300 mole SDS/mole albumin) which, on the other hand, substantially inactivated the bilirubin oxidase after only a very short period of time. With smaller detergent concentrations, an improvement of the dissolving off from the albumin is admittedly found in comparison with a detergent-free reagent but the complete liberation of the albumin-bound bilirubin is not achievable in an incubation time acceptable for routine analyses (for example less than 30 minutes).

Furthermore, in the case of using such detergents, it has been found that a considerable reaction drift of up to 2 hours occurs, which is dependent upon the sample. This also prevents the use of the process for the enzymatic determination of total bilirubin in routine diagnosis.

It is an object of the present invention to provide a process for the determination of total bilirubin which does not suffer from the above-mentioned disadvantages, is simple to carry out and can be automated and, even in the case of a high proportion of albuminbound bilirubin in the sample, provides correct results.

This object is achieved according to the present invention by a process for the determination of total bilirubin in body fluids by means of bilirubin oxidase, wherein the sample is incubated with subtilisin.

Subtilisin (EC 3.4.21.14) includes serine proteases which can be isolated, for example, from *Bacillus subtilis* (subtilopeptidase A) or from related bacteria (subtilopeptidases B and C) (M. Ottensen and I. Svendsen, Methods in Enzymology, 19, 199–215/1970, Biochem.-Biophys. res.Comm. 34 (1969) 600, J. Bacteriol, 94 (1967) 1124, Nature 221, (1969) 235).

That total bilirubin can be determined with the process according to the present invention is especially surprising since, by the addition of other proteases, for example pronase P, endoproteinase Arg C, papain, bromelain, trypsin or chymotrypsin, it is not possible to determine bilirubin completely. Furthermore, in the case of the use of these proteases, there is observed a reaction drift as well as a deactivation of the bilirubin oxidase, presumably due to proteolysis.

In contradistinction thereto, subtilisin completely liberates bilirubin from its albumin binding in a surprisingly short time and after a short time (about 1 minute) no reaction drive is observed.

Furthermore, in spite of the protease activity of subtilisin, bilirubin oxidase is, surprisingly, not deactivated, at least in a period of time of 30 minutes at 37° C. The reason for this is not known.

The process according to the present invention is carried out by incubating the sample, for example plasma or serum, with subtilisin. The period of incubation can hereby be varied within wide limits. The necessary minimum incubation time is essentially dependent upon the temperature and is, for example, at 20° C. not more than about 5 minutes and at 37° C. about 3 minutes. Longer incubation times, for example of 20 or 30 minutes, are also possible without the measurement results being changed.

After incubation has taken place, bilirubin oxidase is added and the total bilirubin is determined. For the determination, there can, in particular, be used:

(a) measurement of the extinction decrease of the bilirubin absorption bands (between about 410 and 480 nm) (see Selected Topics, loc. cit.; and European Patent Specification No.0.005,637);

(b) measurement of the oxygen consumption during the bilirubin oxidation; and (c) measurement of the coloured material formation in the presence of MBTH (see Federal Republic of Germany Patent Specification No. 34 36 005).

If, instead of a water-providing bilirubin oxidase, there is used one giving rise to hydrogen peroxide, the determination can also be based upon the measurement of hydrogen peroxide, for example colorimetrically by the catalase-catalysed formation of formaldehyde from methanol and production of a dihydrolutidine coloured material from the formaldehyde in the presence of ammonium ions and acetylacetone or by the oxidative coupling of MBTH-S with phenols, anilines, naphthols or naphthylamines in the presence of peroxidase. The determination is carried out especially preferably according to method a) above.

In a preferred embodiment, subtilisin and bilirubin oxidase are simultaneously incubated with the sample. The bilirubin content is then, for example, determined by the difference between the initial extinction and the extinction measured after the incubation. for calibration, there is simultaneously used a standard with a known content of bilirubin.

The nature and concentrations of the reaction components, as well as the reaction conditions, such as pH value and buffer capacities, in the case of the process according to the present invention correspond to the statements made hereinafter with regard to the reagent according to the present invention.

The present invention also provides a reagent for the determination of total bilirubin, comprising an aqueous buffered solution containing bilirubin oxidase and, possibly separate therefrom, subtilisin.

The pH value of the aqueous solution is from 4.5 to 9.5 and preferably from 6 to 9. for the adjustment of the pH value, there can be used all buffer substances, the pH values of which are such that, they display a sufficient buffer capacity.

Phosphate, Tris, tricine, Hepes, MES (2-Morpholinoethansulfonicacid) and acetate buffers are especially preferred. The concentration of the buffer substances can be from 0.01 to 1 mole/litre and preferably 0.05 to 0.2 mole/litre. These statements of concentration, as well as all other statements of concentration mentioned herein, including the enzyme activities, are end concentrations in the test.

Subtilisin is preferably used with an activity of from 1 to 50 U/ml., more preferably of from 2 to 20 U/ml. and most preferably of from 5 to 10 U/ml.

Bilirubin oxidase (obtainable, for example, from Takara Shuzo, Japan) is preferably used with an activity of from 0.005 to 20 U/ml. and more preferably of from 0.05 to 5 U/ml.

A preferred reagent according to the prsent invention contains, in a buffered aqueous solution 0.05-5 U/ml. bilirubin oxidase 0.05-0.2 mole/litre buffer substance, pH 6-9 and possibly separate threrefrom 2-20 U/ml. subtilisin.

In another embodiment, the said reaction components are present impregnated into or on to at least one carrier material. As carrier material, there can be used an absorbent or swellable or film-forming carrier material, for example a carrier material known for test strips, such as paper and the like fleece materials, such as tea bag paper or glass fibre fleece. The reaction components can thereby be distributed over several carriers which are in contact with one another. It has proved to be especially advantageous when one carrier contains subtilisin and another carrier in contact therewith contains bilirubin oxidase.

Figure 2:
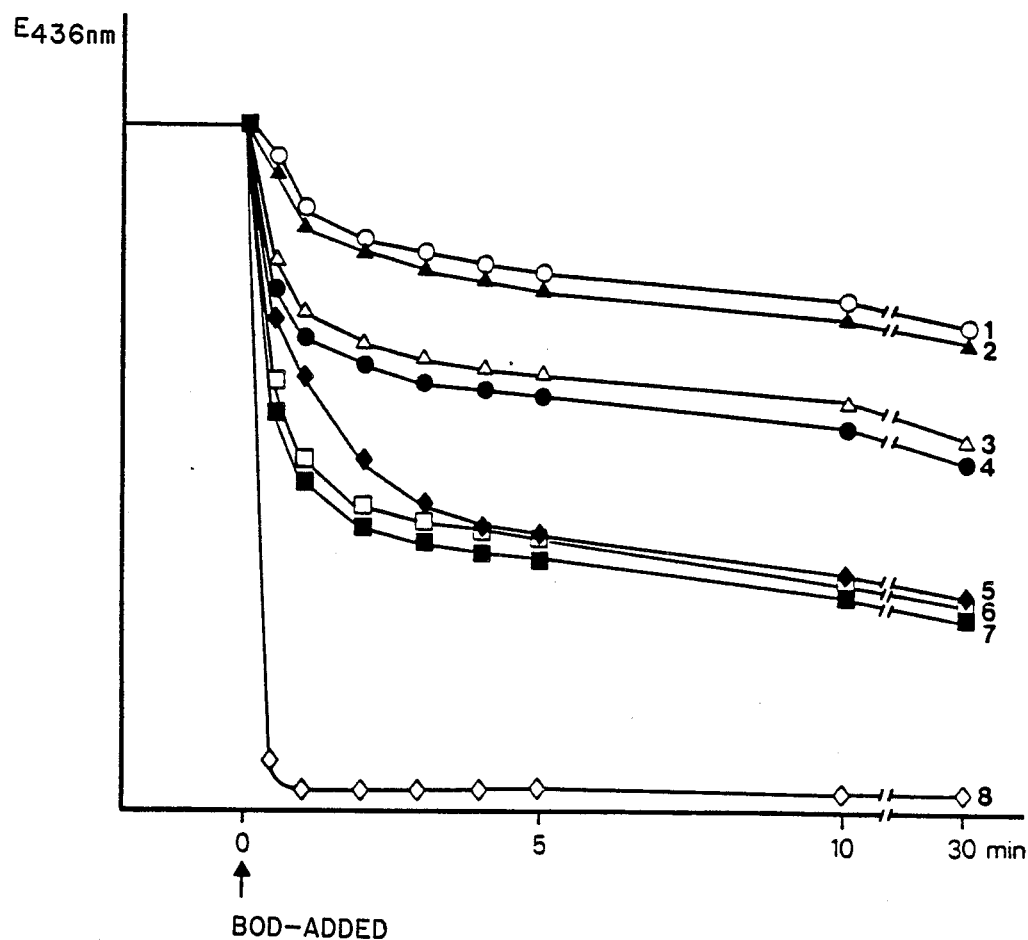

The following Examples are given for the purpose of illustrating the present invention, reference thereby being made to the accompanying drawings, in which:

FIG. 1 shows a method comparison between the process according to the present invention and the DPD method (Scand. J. Clin. Lab. Invest., v. supra); and FIG. 2 shows a comparison of the reaction drift for the bilirubin determination by means of bilirubin oxidase in the case of the addition of proteases/detergent.

EXAMPLE 1

Determination of total bilirubin (1-step test)

30 μl. of sample (serum or standard) and 500 μl. of buffer (0.05 mole/litre sodium phosphate, pH 7.5) are pipetted together. The extinction of the solution is determined at 436 nm. The reaction is started by the addition of 50 μl. of a mixture of subtilisin and bilirubin oxidase (subtilisin end concentration 10 U/ml.; bilirubin oxidase end concentration 0.1 U/ml.).

After incubation for 10 minutes at 37° C., the extinction is again measured at 436 nm. From the difference of the initial and end extinctions, there is calculated the bilirubin concentration of the sample via a factor which is determined by means of a simultaneously used standard of known bilirubin content.

EXAMPLE 2

Determination of total bilirubin (2-step test)

20 μl. of subtilisin solution (end concentration 10 U/ml.) are pipetted into 30 μl. of sample (serum or standard) and 500 μl. of buffer (0.05 mole/litre sodium phosphate, pH 7.5). After incubationfor 10 minutes at 37° C., the extinction is determined at 436 nm. The reaction is started by the addition of 30 μl. bilirubin oxidase (end concentration 0.1 U/ml.). After 5 minutes, the extinction is again read off at 436 nmand from the difference between the initial and end extinctions there is calculated the bilirubin content of the sample via a factor which is determined by means of a simultaneously used standard of known bilirubin content.

EXAMPLE 3

Comparison with the DPD method

With different serum samples, there was compared the bilirubin according to Example 2 and according to the DPD method (Monotest ®10 Boehringer Mannheim GmbH, Order No. 12394). FIG. 1 of the accompanying drawings shows the results obtained. The correlation coefficient is R=0.985. As regression equation there was obtained y=1.13 x−0824.

EXAMPLE 4

Measurement value change in the case of using different proteases

In a determination carried out according to Example 2, instead of subtilisin there were used the following proteases (see FIG. 2):
curve 1: without proteases
curve 2: endo-protease Arg C, 4 mg./ml.
curve 3: papain, 4 mg./ml.
curve 4: bromelain, 4 mg./ml.
curve 5: trypsin, 20 mg./ml.
curve 6: chymotrypsin, 4 mg./ml.
curve 7: SDS, 0.1%
curve 8: Example 2 (comparison measurement).

From FIG. 2, it can be seen that with SDS the effect according to the present invention cannot be achieved. With other serine proteases, for example trypsin or chymotrypsin, no noticeable reduction of the reaction drift can be achieved. Furthermore, these proteases have the disadvantage that they additionally also attack the bilirubin oxidase and thus falsify the measurement result.

It will be understood that the specification and examples are illustrative but not limitative of the present invention and that other embodiments within the spirit and scope of the invention will suggest themselves to those skilled in the art.

What is claimed is:

1. Process for determining total bilirubin content in a body fluid sample comprising incubating said body fluid sample with both subtilisin under conditions favoring complete liberatin of bilirubin bound to albumin from said albumin and with bilirubin oxidase and colorimetrically detecting the products quantitatively formed from bilirubin as a result of bilirubin oxidase activity as a measurement of total bilirubin content in said body fluid sample.

2. The process of claim 1, comprising incubating said sample with subtilisin in the presence of bilirubin oxidase.

3. The process of claim 1 comprising incubating said sample with subtilisin before introducing bilirubin oxidase to the sample 4. The process of claim 1, wherein the subtilisin has activity of from 1 U/mol to 50 U/ml.

5. The process of claim 1, wherein the incubation is carried out in an aqueous buffer solution with a pH of from 4.5 to 9.5.

6. The process of claim 5, wherein the aqueous buffered solution is a buffer selected from the group consisting of phosphate, Tris, tricine, Hepes, MES, and acetate buffer.

7. The process of claim 1, comprising incubating at a temperature in the range of about 20° C. to about 37° C. and for about 5 minutes.

8. A reagent for the determination of total bilirubin in samples of body fluids by reaction with bilirubin oxidase and measuring a result of the reaction, comprising 0.005–20 U/ml bilirubin oxidase, 0.01–1.0 mole/liter buffer substance, pH 4.5–9.5 and, 1–50 U/ml subtilisin.

9. The reagent of claim 8. comprising 0.05 –5 U/ml bilirubin oxidase, 0.05–0.2 mole/liter of said buffer substance, pH 4.5–9.5 and 2–20 U/ml subtilisin.

10. The reagent of claim 8, further comprising at least one absorbent, swellable or film-forming carrier material.

* * * * *